(12) United States Patent
Learmonth et al.

(10) Patent No.: US 10,024,717 B2
(45) Date of Patent: Jul. 17, 2018

(54) TAG READING USING TARGETED SPATIAL SPECTRAL DETECTION

(71) Applicant: TruTag Technologies, Inc., Kapolei, HI (US)

(72) Inventors: Timothy Learmonth, Berkeley, CA (US); Mark Hsu, Richmond, CA (US); Denis Ivanov, Pleasant Hill, CA (US)

(73) Assignee: TruTag Technologies, Inc., Kapolei, HI (US)

(*) Notice: Subject to any disclaimer, the term of this patent is extended or adjusted under 35 U.S.C. 154(b) by 0 days.

(21) Appl. No.: 15/348,873

(22) Filed: Nov. 10, 2016

(65) Prior Publication Data

US 2017/0146402 A1 May 25, 2017

Related U.S. Application Data

(60) Provisional application No. 62/259,244, filed on Nov. 24, 2015.

(51) Int. Cl.
*G01N 21/25* (2006.01)
*G01J 3/28* (2006.01)
*G01J 3/26* (2006.01)

(52) U.S. Cl.
CPC ............... *G01J 3/2803* (2013.01); *G01J 3/26* (2013.01); *G01J 3/28* (2013.01); *G01J 3/2823* (2013.01); *G01J 2003/284* (2013.01); *G01J 2003/2813* (2013.01); *G01J 2003/2826* (2013.01); *G01J 2003/2833* (2013.01); *G01J 2003/2859* (2013.01); *G01J 2003/2866* (2013.01); *G01J 2003/2879* (2013.01)

(58) Field of Classification Search
CPC .... G01J 3/2803; G01J 3/26; G01J 3/28; G01J 3/2823; G01J 2003/2813; G01J 2003/2826; G01J 2003/284; G01J 2003/2859; G01J 2003/2866; G01J 2003/2879; G01T 1/1644; G01N 21/25; G01N 33/483; G02B 5/28; A61B 5/0071; G06K 9/00
See application file for complete search history.

(56) References Cited

U.S. PATENT DOCUMENTS

| | | | | |
|---|---|---|---|---|
| 2008/0317311 | A1* | 12/2008 | Grass | G01T 1/1644 382/131 |
| 2012/0206813 | A1* | 8/2012 | Bahat | G01J 3/26 359/578 |
| 2014/0346235 | A1* | 11/2014 | Learmonth | G06K 19/06 235/489 |

FOREIGN PATENT DOCUMENTS

| WO | 2010019515 | | 2/2010 | |
|---|---|---|---|---|
| WO | WO 2010019515 | A2 * | 2/2010 | ............ A61B 5/0071 |

* cited by examiner

*Primary Examiner* — Jamil Ahmed
(74) *Attorney, Agent, or Firm* — Van Pelt, Yi & James LLP (57) ABSTRACT

A system for determining a spectrum includes an interface and a processor. The interface is configured to receive a sample set of intensity data for an array of spatial locations and a set of spectral configurations. The processor is configured to determine a region of interest using the sample set of intensity data and determine a spectral peak for the region of interest.

24 Claims, 9 Drawing Sheets

TAG READING USING TARGETED SPATIAL SPECTRAL DETECTION

CROSS REFERENCE TO OTHER APPLICATIONS

This application claims priority to U.S. Provisional Patent Application No. 62/259,244 entitled TAG READING USING TARGETED SPATIAL SPECTRAL DETECTION filed Nov. 24, 2015 which is incorporated herein by reference for all purposes.

BACKGROUND OF THE INVENTION

Normally hyperspectral imaging is used for object detection, such as diseased crops, military targets, or geological formations. In those cases once the objects are detected, the job is done. So the number of frames in the hyperspectral cube is set at just enough to ensure that the detection job can be done. However for determining spectra, location and decoding must be achieved. So, just detection is not sufficient. Location and decoding require a much larger amount of data than detection, creating a problem where the storage and processing capabilities of the reader are challenged.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A system for determining a spectrum comprises an interface and a processor. The interface is configured to receive a sample set of intensity data for an array of spatial locations and a set of spectral configurations, where each spectral configuration detects a different wavelength or combination of wavelengths of light. The processor is configured to determine a region of interest using the sample set of data and determine a spectral peak for the region of interest.

In some embodiments, for spectral decoding, both finding an object and decoding a reflected spectrum is required. Memory, time, and/or processing power can be saved by splitting the operations of detection and extraction/decoding.

In some embodiments, for determining a spectrum, memory can be saved by processing frames as they appear without saving them, so that the full set of frames required for spectral detection doesn't have to be kept in memory. For example, objects (e.g., tags) can be found by looking for local maxima in the standard deviation of received intensity values along the spectral axis. In another example, objects (e.g., tags) can be found by looking for peaks by looking for maxima after filtering input data (e.g., running a convolutional filter—for example, a matched filter with suppression in the surround). In some embodiments, filtering and looking for a maxima in standard deviation are done in sequence to identify a region of interest. In some embodiments, filtering and looking for peaks in two ranges of frequencies are done in sequence to identify a region of interest. In this case each frame is a digitized image of a sample collected at a specific wavelength or set of wavelengths, and different frames are collected using different wavelengths or set of wavelengths. To calculate the standard deviation, the sum of the frames and the sum of the square of the frames are needed. So when a frame appears, each intensity value in each location of the frame and its square are each added to an accumulator. Each frame is then overwritten by the next frame. Once all the frames are collected, a simple operation is performed on the two accumulated values (e.g., the sum and the sum of the squares) for each location in the frame to get the standard deviation of the value in that location of the frame. In this manner, a new frame (e.g., a map) is created that has the same spatial dimensions as the original frames but contains the standard deviation through the frames at each point. Then local maxima in the map correspond to locations of candidate tags on the full hyperspectral cube. In various embodiments, this method is applied either to a full hypercube as the hypercube is captured or to a subset of a hypercube.

In some embodiments, spectral detection is achieved using filtering along the spectral axis, assuming that the filter kernel is shorter than the full spectral axis. With filtering, a subset of frames equal to the kernel length is kept in memory at one time, rather than just the one for the standard deviation. This is what we're calling sequential processing. To determine the kernel length used for this step, we find the minimum number of frames sufficient to detect an object reliably by isolating a spectral feature in the filtering approach. For example, in the event that the filter kernel is tuned to couple strongly to a spectral feature with spectral width equal to 1/10 the length of the full spectral axis, the kernel length might be 1/10 the full spectral axis length. Or it could be done by capturing a subset of many spectral features in the standard deviation approach. For example, the targeted spectral features might be a set of strong peaks or valleys in the spectrum that serve to increase the standard deviation along the spectral axis. Also in the event that memory isn't a constraint, the frames in this step could be stored in memory and reused in the last step below. In that case processing power is saved by not processing the entire hyperspectral cube, and time is saved, by computing the regions of interest while capture of the hyperspectral cube is still ongoing. At the end of the sequential processing, a 2D array has been determined over the spatial axes that has a higher value where candidate objects are present, and a lower value where they are not. From this array, regions of interest are chosen that are likely to contain an object. For example, regions of interest may be chosen by searching the 2D array for maxima (points where all neighbors are less than the point itself). Maxima may then be sorted in descending order of value, creating a list of points, with the first in the list most likely to correspond to a tag, the second in the list the second most likely, etc. Regions of interest can then be determined by including a fixed range of points around each point in the list, with the size of the range determined from the expected size of an object. The regions of interest are then the focus for analysis.

In some embodiments, at this point a full scan is run to extract spectral information with enough frames to extract the object information. But during the data collection, only the hyperspectral information in the regions of interest is saved. This greatly reduces the amount of data saved in memory. For example, in the event that the objects comprise 1% of the reader field of view, a data reduction on the order of 99% can be achieved in this manner.

In some embodiments, the data collected is not a computed spectrum, so further processing is necessary to obtain a spectrum from the data collected. In the event that the reader is based on a Fabry-Perot Interferometer in a low-finesse Fourier Transform mode, for example, then conversion from captured data to a spectrum requires a Fourier transform. If only the regions of interest are processed into spectra, the computational effort required to decode a spectrum of an object is further reduced. Once a spectrum from an object such as a tag is obtained, decoding can proceed. In some embodiments, a tag comprises a reflector with selective reflection. In various embodiments, the reflector comprises one or more of the following: a rugate tag, a Bragg reflector, or any other appropriate reflector. In various embodiments, tags comprise one of the following materials: silicon, silicon dioxide, silicon nitride, doped silicon, or any other appropriate material. In some embodiments, the unique optical signature of each tag can be read using an absolute or a relative spectral measurement device, apparatus, or system. In some embodiments, tags comprise the surface of a silicon wafer that is etched to have a spectral code encoded by the etching. A thin layer from the surface of the etched wafer is removed and divided into small tags, and the resultant tags contain a complex porous nanostructure that is programmed during electrochemical synthesis to display a unique reflectivity spectrum. The tags are then oxidized by a high-temperature bake step to turn the crystalline, nanoporous silicon tags into amorphous, nanoporous silica. This bake step stabilizes the nanoporous structure against further oxidation (thus stabilizing the spectral signature) and provides for the tags to be characterized as a GRAS excipient.

In some embodiments, spectral configuration detects a different wavelength or combination of wavelengths of light by spectral filtering reflected light from an object before detecting the light in a detector. In various embodiments, the spectral filtering comprises a Fabry-Perot filter, an interference filter, or any other appropriate spectral filter. In some embodiments, the spectral filter is tunable. In some embodiments, the spectral filter is a set of fixed filters that are in front of separate detectors or are mechanically swapped or optically switched in front of a fixed detector. In various embodiments, the Fabry-Perot filter is mechanically tunable, electro-optically tunable (e.g., a change in index of refraction of the medium in between the partially reflecting mirrors), acousto-optically tunable, or any other appropriate filter.

Figure 1:
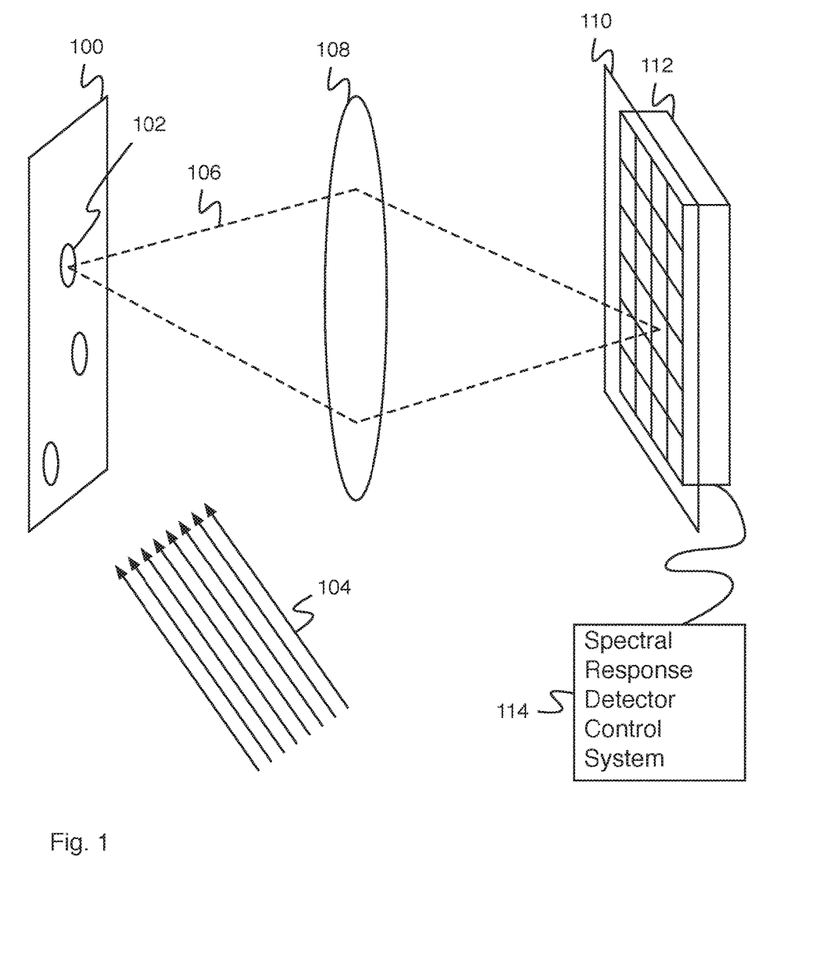
FIG. 1 is a diagram illustrating an embodiment of an optical setup for spectral response detection.

FIG. 1 is a diagram illustrating an embodiment of an optical setup for spectral response detection. FIG. 1 comprises measurement area 100 comprising one or more regions for producing optical spectra (e.g., region 102). Measurement area 100 is illuminated by light 104. Reflected light 106 comprises light reflected by region 102. Reflected light 106 is focused by lens 108, passes through filter 110, and is captured by optical detector 112. Filter 110 comprises a filter for transmitting light at some frequencies and not at other frequencies. Optical detector 112 comprises an optical detector for detecting optical intensities. Spectral response detector control system 114 comprises a spectral response detector control system for interacting with optical detector 112. Spectral response detector control system 114 provides control information to optical detector 112 (e.g., control information indicating to capture data) and receives optical intensity data from optical detector 112.

In some embodiments, regions for producing optical spectra (e.g., region 102) comprise optical tags (e.g., optical tags engineered to reflect light with a recognizable spectrum). In various embodiments, light 104 comprises broadband light, narrowband light, filtered light, light from a light-emitting diode, laser light, or any other appropriate light. In various embodiments, light 104 is incident to measurement area 100 from a single point, at a single angle, from multiple angles, or incident in any other appropriate manner. In some embodiments, filter 110 comprises a tunable optical filter. In some embodiments, filter 110 comprises a Fabry-Perot interferometer. In some embodiments, optical detector 112 comprises an array of optical detector pixels for detecting an array of optical intensities. In some embodiments, the array of optical detector pixels comprises an x axis and a y axis. In some embodiments, each pixel of the array of optical detector pixels comprises a set of optical detectors, each optical detector comprising a color filter (e.g., each pixel comprises three detectors, a first detector comprising a red color filter, a second detector comprising a green color filter, and a third detector comprising a blue color filter). In some embodiments, spectral response detector control system 114 interacts with filter 110 (e.g., to indicate tunable filter properties). In some embodiments, spectral response detector control system 114 interacts with filter 110 to indicate a Fabry-Perot interferometer gap size. In some embodiments, spectral response detector control system 114 is configured to receive a calibration data. In some embodiments, the calibration data comprises a set of intensity data for an array of spatial locations and a range of spectral configurations for a monochromatic source (e.g., a set of gap sizes for a Fabry-Perot interferometer).

Figure 2:
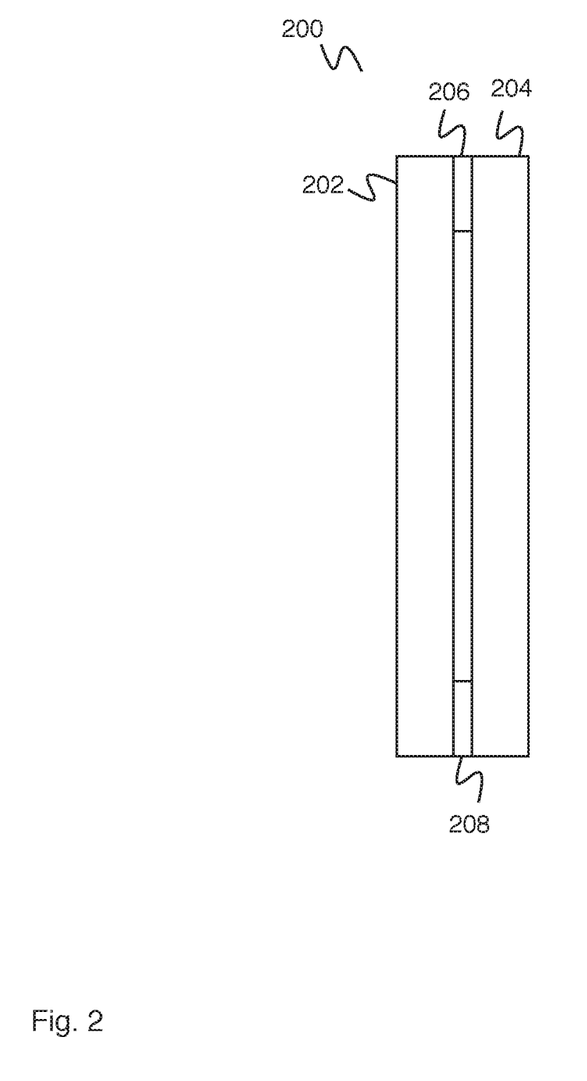
FIG. 2 is a diagram illustrating an embodiment of a Fabry-Perot interferometer.

FIG. 2 is a diagram illustrating an embodiment of a Fabry-Perot interferometer. In some embodiments, Fabry-Perot interferometer 200 comprises filter 110 of FIG. 1. Fabry-Perot interferometer 200 comprises mirror 202 and mirror 204. Each of mirror 202 and mirror 204 comprises a partially reflective mirror (e.g., some light is able to pass through and some light is reflected). Each of mirror 202 and mirror 204 comprises a mirror silvering on one side (e.g., mirror 202 comprises a mirror silvering on its right side as shown in FIG. 2 and mirror 204 comprises a mirror silvering on its left side as shown in FIG. 2). Mirror 202 and mirror 204 are held together by piezo element 206 and piezo element 208. Piezo element 206 and piezo element 208 comprise piezo elements for changing size. Piezo element 206 and piezo element 208 change size according to an applied voltage. When piezo element 206 and piezo element 208 change size, the gap between the mirror silvering of mirror 202 and the mirror silvering of mirror 208 changes. Changing the gap between the mirror silvering of mirror 202 and the mirror silvering of mirror 208 causes the optical properties (e.g., the light transmission and reflectance properties) of Fabry-Perot interferometer 200 to change. In this way, Fabry-Perot interferometer 200 comprises a tunable optical filter.

In some embodiments mirror silvering comprises a partially reflective metal layer (e.g., a silver layer, an aluminum layer, a titanium layer, etc.). In various embodiments, mirror 202 and mirror 204 are held together by 1, 2, 3, 4, 5, or any other appropriate number of piezo elements. In some embodiments, the spatial positioning of the piezo elements separating mirror 202 and mirror 204 enable adjustment of the angle between mirror 202 and mirror 204.

In some embodiments, the mirrors are separated with a fixed distance and a medium interior to the mirrors changes its index of refraction (e.g., electro- or acousto-optically) and instead of a set of gap sizes there is a set of different index-changed path lengths.

Figure 3:
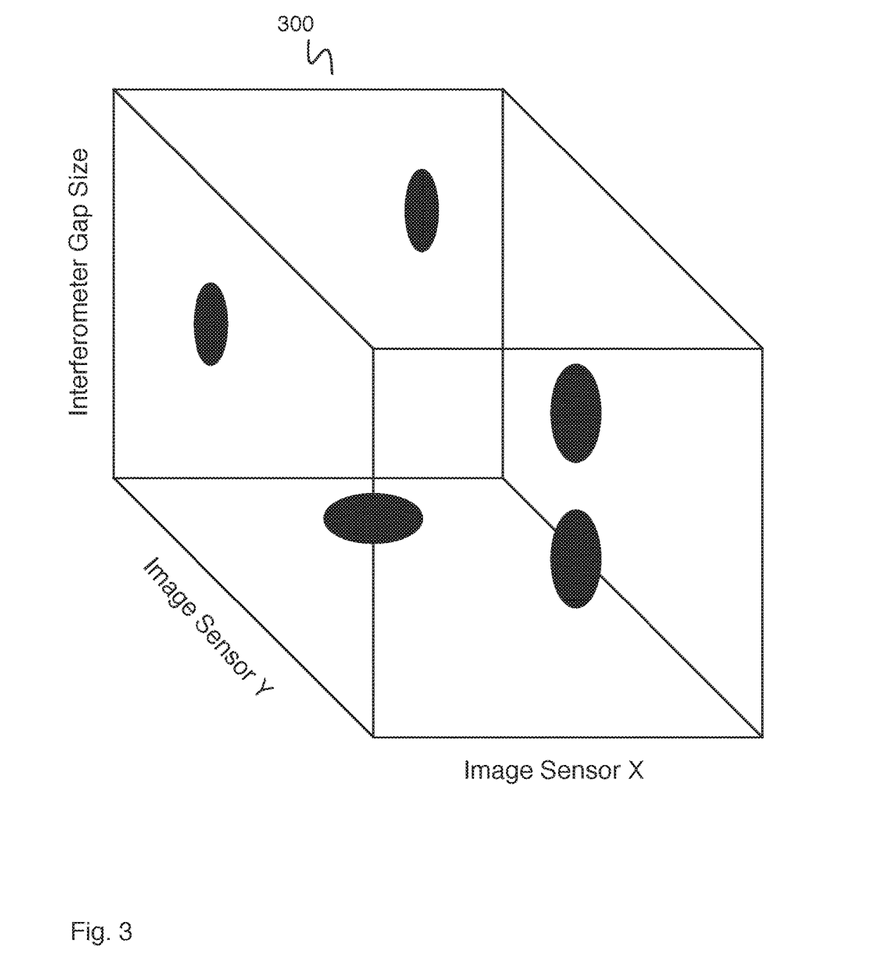
FIG. 3 is a diagram illustrating an embodiment of a spectral data cube.

FIG. 3 is a diagram illustrating an embodiment of a spectral data cube. In some embodiments, spectral data cube 300 of FIG. 3 comprises a cube representing data measured by an optical detector (e.g., optical detector 112 of FIG. 1). Spectral data cube 300 comprises a cube of data recorded by an optical detector. The x axis of spectral data cube 300 corresponds to the x axis of the optical detector and the y axis of spectral data cube 300 corresponds to the y axis of the optical detector. The z axis of spectral data cube 300 corresponds to an interferometer gap size (e.g., the mirror gap size of a Fabry-Perot interferometer). The data intensity shown at a given data location (e.g., corresponding to a given x and y location on the optical detector and a given interferometer gap size) indicates the intensity of the light received by the optical detector.

In some embodiments, the interferometer gap size comprises the gap size of Fabry-Perot interferometer 200 of FIG. 2. In various embodiments, spectral data cube 300 comprises a spectral data hypercube with one or more of the following properties: each data location comprising three light intensity measurements, each measurement taken by a separate optical detector at the given location, each optical detector associated with a different color filter, or any other appropriate properties. In some embodiments, multiple peaks associated with different interferometer gap sizes are measured at a given detector location.

Figure 4:
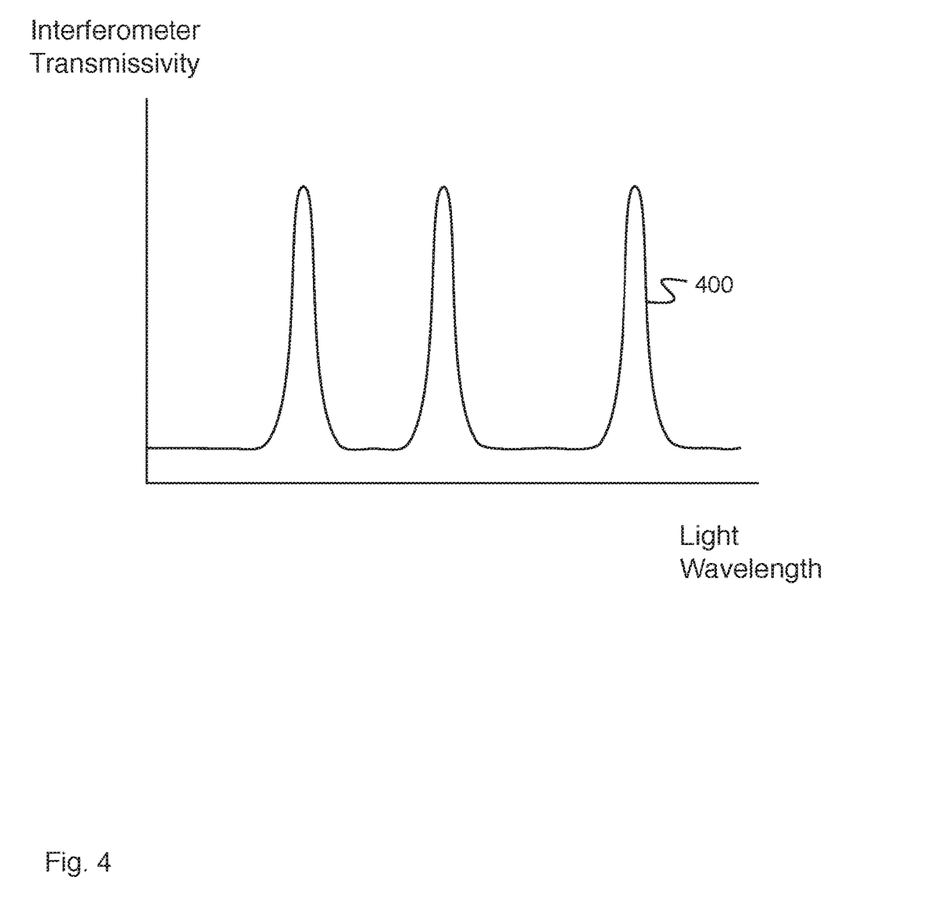
FIG. 4 is a diagram illustrating an embodiment of interferometer transmissivity.

FIG. 4 is a diagram illustrating an embodiment of interferometer transmissivity. In some embodiments, curve 400 of FIG. 4 illustrates the light transmissivity of a Fabry-Perot interferometer (e.g., Fabry-Perot interferometer 200 of FIG. 2) vs. light wavelength. In the example shown, curve 400 of FIG. 4 illustrates the light transmissivity of a Fabry-Perot interferometer vs. light wavelength for a given gap size. Multiple light transmission peaks are seen for the given gap size. Three light transmission peaks are seen in curve 400. In various embodiments, two light transmission peaks are seen as a function of gap size, three light transmission peaks are seen as a function of gap size, four light transmission peaks are seen as a function of gap size, or any other appropriate number of light transmission peaks are seen as a function of gap size.

Figure 5:
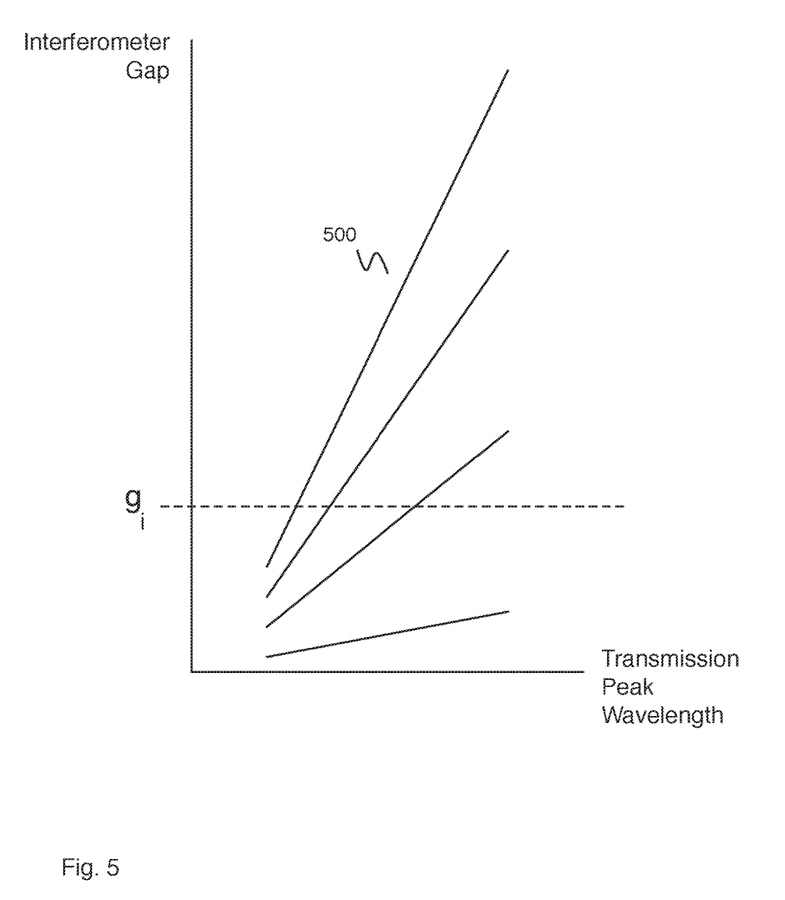
FIG. 5 is a diagram illustrating an embodiment of interferometer transmission peak wavelength locations.

FIG. 5 is a diagram illustrating an embodiment of interferometer transmission peak wavelength locations. In some embodiments, set of curves 500 illustrates a set of transmission peak locations for a Fabry-Perot interferometer (e.g., Fabry-Perot interferometer 200 of FIG. 2). In the example shown, set of curves 500 illustrates the location of each of a set of interferometer transmission peak locations as the interferometer gap of the Fabry-Perot interferometer is changed. In the example shown, set of curves 500 comprises 4 curves. For a given gap size (e.g., gap size $g_i$), there are a set of transmission peaks at different wavelengths (e.g., as shown by curve 400 of FIG. 4).

Figure 6A:
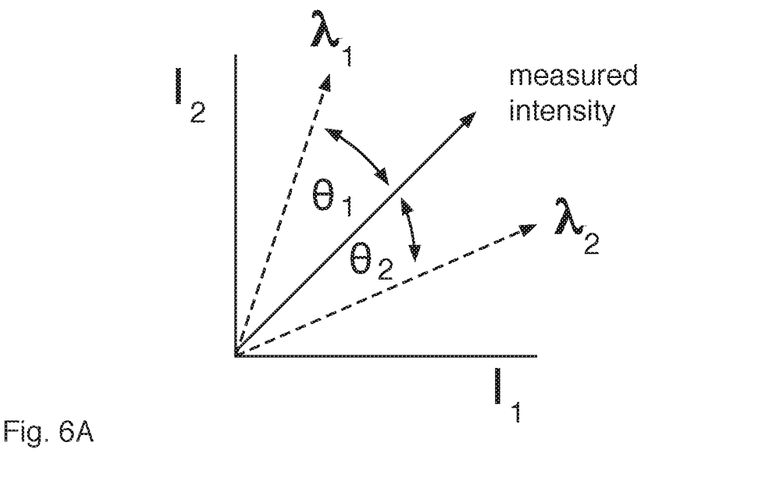
FIG. 6A is a diagram illustrating an embodiment of vectors in a parameter space.

FIG. 6A is a diagram illustrating an embodiment of vectors in a parameter space. In some embodiments, the vectors of FIG. 6A are two dimensional representations of intensity vectors (e.g., vectors comprising a first color intensity in a first direction as measured by a first color detector and a second color intensity in a second direction as measured by second color detector). In some embodiments, a vector is calculated and displayed in a three dimensional space (e.g., the three dimensions correspond to three color detectors). In the example shown, vectors $\lambda_1$ and $\lambda_2$ comprise calibration vectors for a Fabry-Perot interferometer (e.g., Fabry-Perot interferometer 200 of FIG. 2). A set of calibration vectors is associated with each gap size of the Fabry-Perot interferometer. Each calibration vector of the set of calibration vectors is associated with a transmission peak associated with the gap size. Determining a calibration vector comprises illuminating the Fabry-Perot interferometer with monochromatic light of the transmission peak wavelength and recording the intensity measured by each optical detector of a set of optical detectors forming a pixel (e.g., each optical detector associated with a different color filter). Each optical detector is associated with an axis of the parameter space. Measured intensity vector 600 comprises a vector associated with an optical measurement. In some embodiments, measured intensity vector 600 comprises a representation of data at one point within data cube 300 of FIG. 3. Angles $\theta_1$ and $\theta_2$ comprise the angles formed between the calibration vectors and measured intensity vector 600.

In various embodiments, intensity vectors comprise intensity vectors in a two-dimensional parameter space (e.g., representing two color intensities), intensity vectors in a three-dimensional parameter space (e.g., representing three color intensities), intensity vectors in a five-dimensional parameter space (e.g., representing five color intensities), or intensity vectors in any other appropriate parameter space.

Figure 6B:
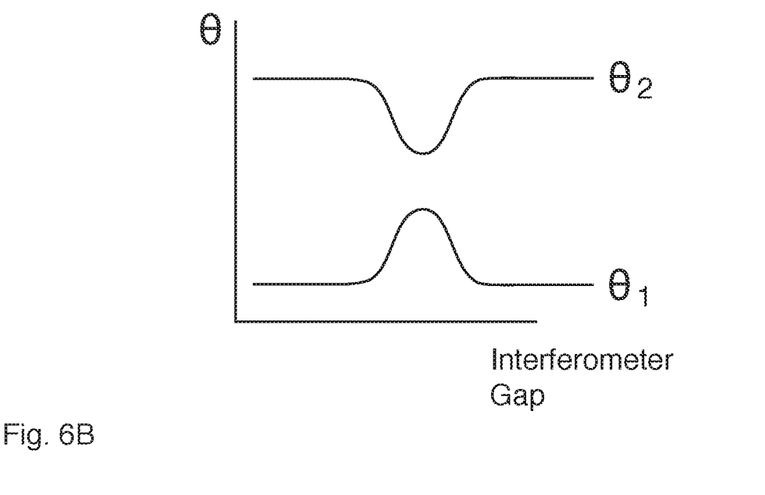
FIG. 6B is a diagram illustrating an embodiment of an angular measurement as a function of interferometer gap.

FIG. 6B is a diagram illustrating an embodiment of an angular measurement as a function of interferometer gap. In the example shown, $\theta_1$ and $\theta_2$ are plotted as an interferometer gap is varied. $\theta_2$ is seen to dip at a gap size of interest, while $\theta_1$ is seen to rise, indicating the measured intensity vector swings toward calibration vector $\lambda_2$. This swing indicates that the measured light is passing through the Fabry-Perot interferometer at the transmission peak associated with calibration vector $\lambda_2$ and not the transmission peak associated with calibration vector $\lambda_1$. In some embodiments, $\theta_1$ and $\theta_2$ comprise $\theta_1$ and $\theta_2$ as shown in FIG. 6A.

In some embodiments, in three dimensions the angles are measured in three dimensions towards calibration vectors. In some embodiments, in the event that the angles shift as a function of gap towards one of the calibration vectors as the gap is incremented or decremented, it is determined that the peak corresponds to the peak associated with the calibration vector.

Figure 7:
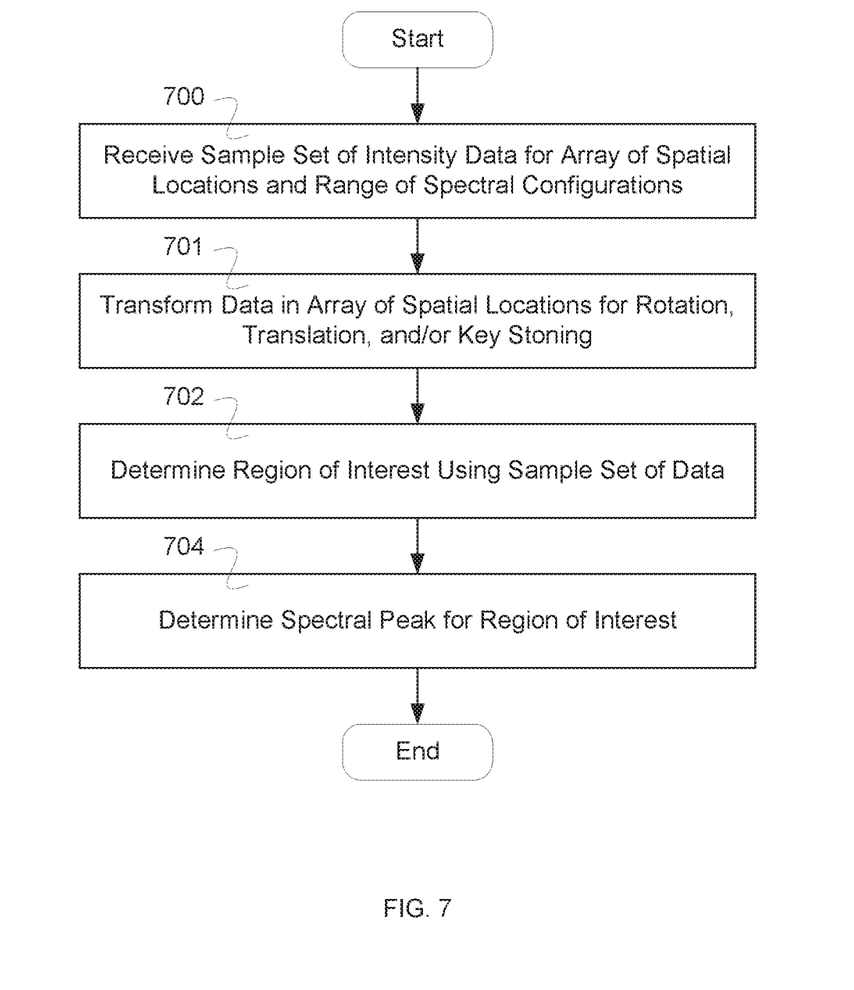
FIG. 7 is a flow diagram illustrating an embodiment of a process for spectral reading using targeted spatial spectral detection.

FIG. 7 is a flow diagram illustrating an embodiment of a process for spectral reading using targeted spatial spectral detection. In 700, a sample set of intensity data is received for an array of spatial locations and a range of spectral configurations. In 701, data in the array of spatial locations is transformed for rotation, translation, and/or key stoning. In 702, a region of interest is determined using the sample set of data. In 704, a spectral peak is determined for the region of interest.

In some embodiments, the process of FIG. 7 is executed by spectral response detector control system 114. In some embodiments, a set of regions of interest is determined in 702. In some embodiments, a spectral peak is determined in 704 for all regions of interest in the set of regions of interest. In some embodiments, more than one spectral peak is determined for a region of interest. In some embodiments, determining one or more spectral peaks comprises decoding a signature. In some embodiments, the signature comprises a tag signature.

In some embodiments, spectral peak is identified within the spatial array of data associated with one spectral configuration. To correspond this peak with a peak identified within the spatial array of data associated with another spectral configuration, in some embodiments, the data of the spatial array is corrected for rotation, translation, and/or keystoning (e.g., trapezoidal scaling). In some embodiments, spatial array data is processed in an area larger than a region of interest to make sure that a peak that is associated with one spectral configuration can be matched to the peak associated with another spectral configuration. For example, a first spatial array of data is taken associated with one spectral configuration and then at a later time a spatial array of data is taken associated with another spectral configuration. Between the two times, it is possible that the data taking device is rotated, translated, and/or tilted making the data in the two corresponding spatial arrays of data related to each other with a rotation, translation, and/or key stoning translation.

Figure 8:
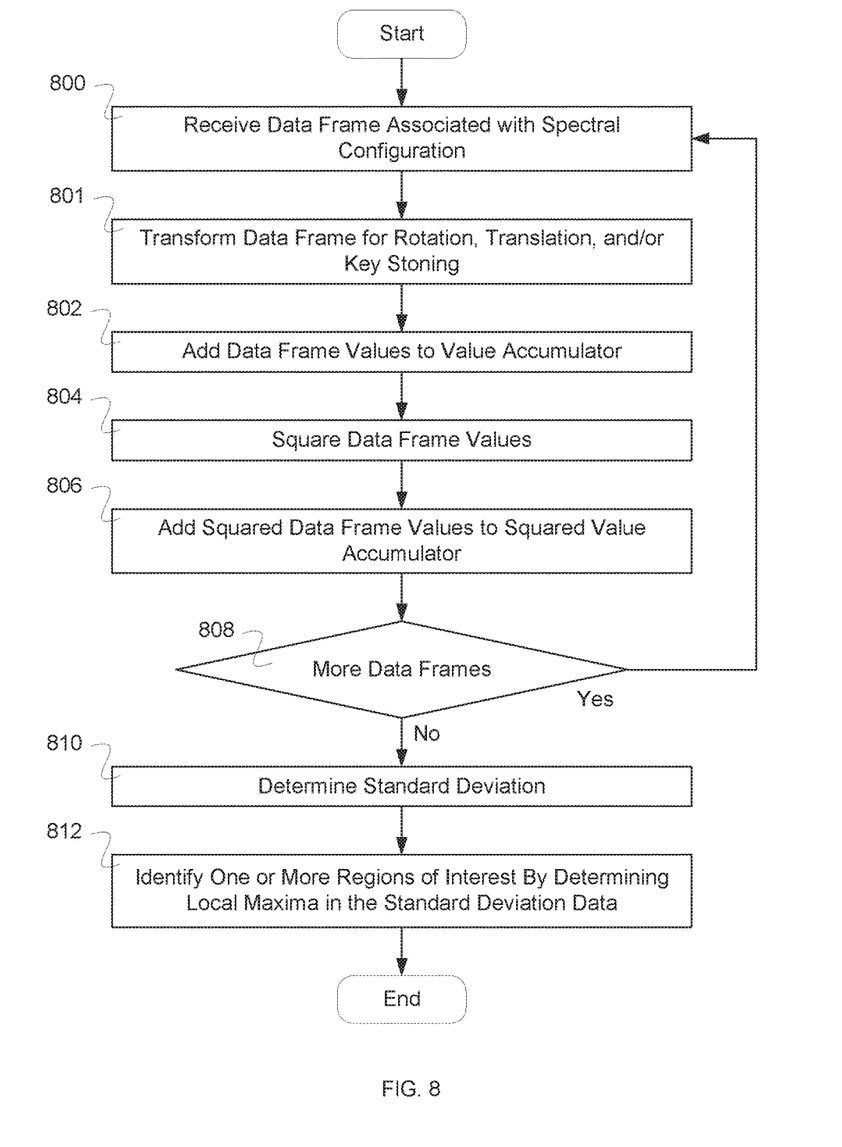
FIG. 8 is a flow diagram illustrating an embodiment of a process for determining a region of interest using a sample set of data.

FIG. 8 is a flow diagram illustrating an embodiment of a process for determining a region of interest using a sample set of data. The flow diagram of FIG. 8 illustrates an embodiment of a process for determining a region of interest using a standard deviation calculation. In 800, a data frame associated with a spectral configuration is received. In 801, data frame is transformed for rotation, translation, and/or key stoning. For example, to get correspondence between spatial arrays of data associated with different spectral configurations, transformation is performed if necessary between spatial arrays to make sure that the data in the arrays are spatially associated with each other. In some embodiments, fiducials in the data frames are used to determine the transformations. In 802, the data frame is added to a value accumulator. In the event the data frame comprises the first data frame, the value accumulator is set to the value of the data frame. In 804, the data frame values are squared (e.g., each value of the data frame values is squared). In 806, the squared data frame values are added to a squared value accumulator. In the event the data frame comprises the first data frame, the squared value accumulator is set to the value of the squared data frame. In 808, it is determined whether there are more data frames. In the event there are more data frames, control passes to 800. In the event there are not more data frames, control passes to 810. In 810, the standard deviation is determined. Determining the standard deviation for a set of data frames comprises determining the standard deviation for each point of the data frame, across the set of data frames. The standard deviation for the set of data frames can be determined by first determining the data mean by dividing the values of the value accumulator by the total number of data frames received. A mean of squared data can additionally be determined by dividing the values of the squared value accumulator by the total number of data frames received. The standard deviation for the set of data frames can then be determined by determining the square root of the difference between the mean of squared data and the square of the data mean. In 812, one or more regions of interest are identified by determining local maxima in the standard deviation data (e.g., local maxima across the data frame).

In some embodiments, the process of FIG. 8 implements 702 of FIG. 7. In some embodiments, a data frame comprises a two-dimensional array of data pixels. In some embodiments, each data pixel comprises three colored pixels, each colored pixel associated with a color filter of a different color. In some embodiments, one or more signal processing techniques other than standard deviation computation are used for processing the spectral axis of the data cube (e.g., thresholding, filtering, matched filtering, etc.).

Figure 9:
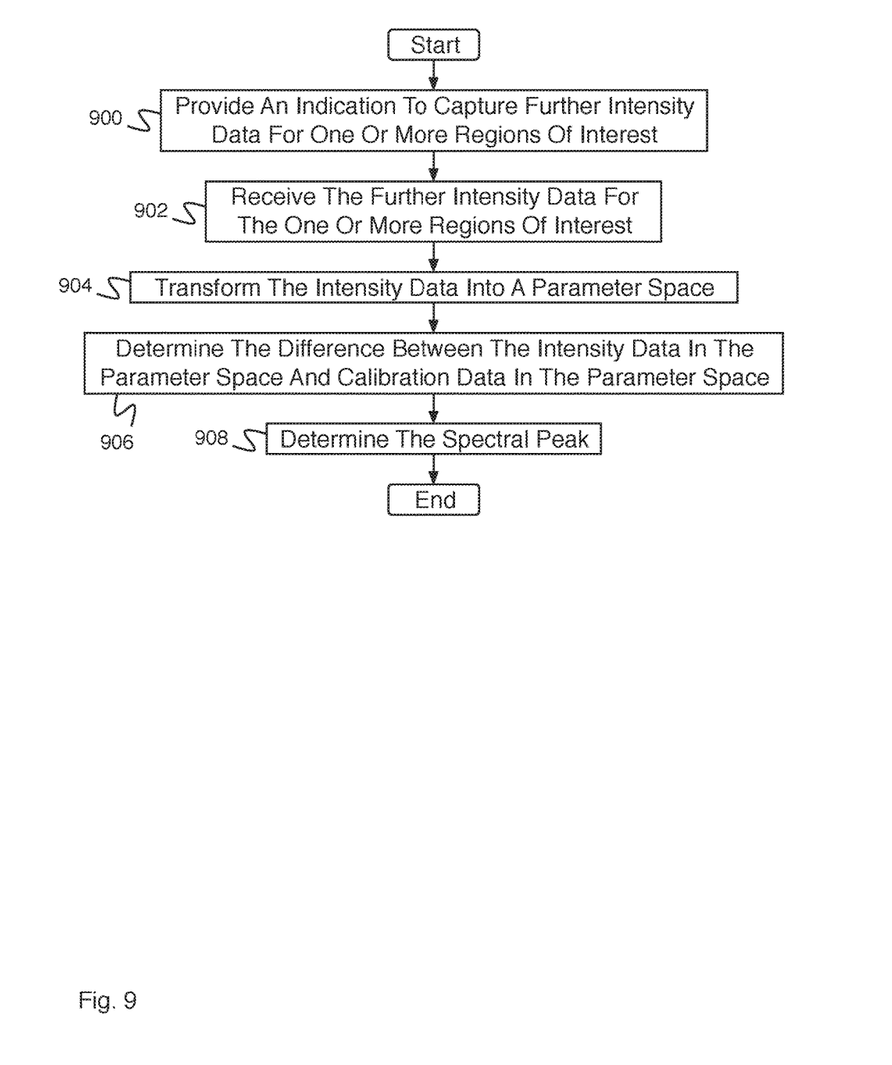
FIG. 9 is a flow diagram illustrating an embodiment of a process for determining a spectral peak for a region of interest.

FIG. 9 is a flow diagram illustrating an embodiment of a process for determining a spectral peak for a region of interest. In some embodiments, the process of FIG. 9 implements 704 of FIG. 7. In 900, an indication to capture further intensity data for one or more regions of interest is provided. In 902, the further intensity data for the one or more regions of interest is received. In 904, the intensity data is transformed into a parameter space (e.g., the parameter space shown in FIG. 6A). In 906, the difference between the intensity data in the parameter space and calibration data in the parameter space is determined. In 908, the spectral peak is determined (e.g., by determining a calibration data vector in the parameter space that the intensity data in the parameter space exhibits a movement towards).

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:
1. A system for determining a spectrum, comprising:
   an interface configured to receive a sample set of intensity data for an array of spatial locations and a set of spectral configurations, wherein the sample set of intensity data for the array of spatial locations and the set of spectral configurations comprises an imaging measurement at each location in the array of spatial locations for each spectral configuration in the set of spectral configurations, wherein each location in the array of spatial locations corresponds to a sample location, wherein the sample comprises an optical tag having a predetermined size, and wherein the optical tag reflects light with a recognizable spectrum;

a processor configured to:
determine a first region of interest using the sample set of intensity data, comprising:
determining a set of locations of the array of spatial locations corresponding to a maxima;
ranking the set of locations based on a likelihood that a location corresponds to the optical tag; and
determining the first region of interest to include a fixed range around the location of the set of locations, wherein the location is ranked most likely to correspond to the optical tag, wherein the fixed range is based at least in part on the predetermined size of the optical tag;
determine one or more spectral peaks for the first region of interest; and
in response to the one or more spectral peaks for the first region of interest being not identified as the recognizable spectrum, determine a second region of interest using the sample set of intensity data and determine one or more spectral peaks for the second region of interest.

2. The system of claim 1, wherein the sample set of intensity data comprises three color intensity data.

3. The system of claim 1, wherein the array of spatial locations comprises a two dimensional array of spatial locations.

4. The system of claim 1, wherein the set of spectral configurations comprises a set of Fabry-Perot interferometer gap sizes.

5. The system of claim 1, wherein the set of spectral configurations comprises a sparse set of gap sizes across a broad gap range.

6. The system of claim 1, wherein the set of spectral configurations comprises a cluster of gap sizes within a predetermined narrow gap range.

7. The system of claim 6, wherein the predetermined narrow gap range is based at least in part on a known reference peak.

8. The system of claim 1, wherein the set of locations of the array of spatial locations is determined using a filter.

9. The system of claim 1, wherein the set of locations of the array of spatial locations is determined using a threshold.

10. The system of claim 1, wherein the set of locations of the array of spatial locations is determined using a calculation of a standard deviation.

11. The system of claim 1, wherein the first region of interest comprises one of a plurality of regions of interest.

12. The system of claim 1, wherein the interface is further configured to receive a calibration data.

13. The system of claim 12, wherein the calibration data comprises a calibration set of intensity data for a calibration array of spatial locations and a calibration set of spectral configurations for a monochromatic source.

14. The system of claim 1, wherein determining the one or more spectral peaks for the first region of interest comprises providing an indication to capture further intensity data for the first region of interest.

15. The system of claim 1, wherein determining the one or more spectral peaks for the first region of interest comprises receiving further intensity data for the first region of interest.

16. The system of claim 1, wherein determining the one or more spectral peaks for the first region of interest comprises:
transforming the intensity data into a parameter space; and
determining a difference between the intensity data in the parameter space and a calibration data in the parameter space.

17. The system of claim 1, wherein the first region of interest comprises one of a set of regions of interest.

18. The system of claim 17, wherein the processor is further configured to determine a set of spectral peaks corresponding to the set of regions of interest.

19. The system of claim 1, wherein the processor is further configured to determine one or more spectral peaks for the second region of interest.

20. The system of claim 1, wherein the processor is further configured to decode a signature.

21. The system of claim 20, wherein the signature comprises a tag signature.

22. A method for determining a spectrum, comprising:
receiving a sample set of intensity data for an array of spatial locations and a set of spectral configurations, wherein the sample set of intensity data for the array of spatial locations and the set of spectral configurations comprises an imaging measurement at each location in the array of spatial locations for each spectral configuration in the set of spectral configurations, wherein each location in the array of spatial locations corresponds to a sample location, wherein the sample comprises an optical tag having a predetermined size, and wherein the optical tag reflects light with a recognizable spectrum;
determining, using a processor, a first region of interest using the sample set of data, comprising:
determining a set of locations of the array of spatial locations corresponding to a maxima;
ranking the locations of the set of locations based on a likelihood that a location corresponds to the optical tag; and
determining the first region of interest to include a fixed range around the location of the set of locations ranked most likely to correspond to the optical tag, wherein the fixed range is based at least in part on the predetermined size of the optical tag;
determining one or more spectral peaks for the first region of interest; and
in response to the one or more spectral peaks for the first region of interest being not identified as the recognizable spectrum, determining a second region of interest using the sample set of intensity data and determining one or more spectral peaks for the second region of interest.

23. A computer program product for determining a spectrum, the computer program product being embodied in a non-transitory computer readable storage medium and comprising computer instructions for:
receiving a sample set of intensity data for an array of spatial locations and a set of spectral configurations, wherein the sample set of intensity data for the array of spatial locations and the set of spectral configurations comprises an imaging measurement at each location in the array of spatial locations for each spectral configuration in the set of spectral configurations, wherein each location in the array of spatial locations corresponds to a sample location of a sample, wherein the sample comprises an optical tag having a predetermined size, and wherein the optical tag reflects light with a recognizable spectrum;

determining a first region of interest using the sample set of data; and data, comprising:

determining a set of locations of the array of spatial locations corresponding to a maxima;

ranking the locations of the set of locations based on a likelihood that a location corresponds to the optical tag; and determining the first region of interest to include a fixed range around the location of the set of locations ranked most likely to correspond to the optical tag, wherein the fixed range is based at least in part on the predetermined size of the optical tag;

determining one or more spectral peaks for the first region of interest; and in response to the one or more spectral peaks for the first region of interest being not identified as the recognizable spectrum, determining a second region of interest using the sample set of intensity data and determining one or more spectral peaks for the second region of interest.

24. The system of claim 1, wherein the second region of interest includes a second location of the set of locations ranked next most likely to correspond to the optical tag.

* * * * *